United States Patent

Klor et al.

[11] Patent Number: 5,886,037
[45] Date of Patent: Mar. 23, 1999

[54] NUTRITIONAL COMPOSITION FOR THE TREATMENT OF HYPERTRIGLYCERIDAEMIA AND HYPERCHYLOMICRONAEMIA

[75] Inventors: Hans-Ulrich Bernhard Klor, Linden; Annette Hauenschild, Lich, both of Germany

[73] Assignee: N.V. Nutricia, Zoetermeer, Netherlands

[21] Appl. No.: 975,074

[22] Filed: Nov. 20, 1997

[30] Foreign Application Priority Data

Nov. 20, 1996 [EP] European Pat. Off. ............. 96203249

[51] Int. Cl.[6] .................... A16K 31/19; A16K 31/20
[52] U.S. Cl. ................. 514/546; 514/547; 514/557; 514/558; 514/560; 424/523; 426/601; 426/602
[58] Field of Search .................. 514/546, 547, 514/557, 558, 560; 424/523; 426/602, 607, 549, 601, 613, 631, 801, 660, 804, 810

[56] References Cited

U.S. PATENT DOCUMENTS

| | | | |
|---|---|---|---|
| 4,678,808 | 7/1987 | Ward et al. | 514/560 |
| 4,752,618 | 6/1988 | Mascioli et al. | 514/549 |
| 4,820,731 | 4/1989 | Mascioli et al. | 514/549 |
| 4,871,768 | 10/1989 | Bistrian et al. | 514/547 |
| 5,000,975 | 3/1991 | Tomarelli . | |
| 5,034,414 | 7/1991 | Wakabayashi et al. | 514/560 |
| 5,288,512 | 2/1994 | Seiden . | |
| 5,444,054 | 8/1995 | Garleb et al. . | |
| 5,574,065 | 11/1996 | Trimbo | 514/546 |
| 5,709,888 | 1/1998 | Gil et al. | 514/560 |

FOREIGN PATENT DOCUMENTS

| | | |
|---|---|---|
| 0 484 266 | 5/1992 | European Pat. Off. . |
| 0 687 418 | 12/1995 | European Pat. Off. . |

*Primary Examiner*—James O. Wilson
*Attorney, Agent, or Firm*—Young & Thompson

[57] ABSTRACT

A nutritional composition comprising fats and optionally carbohydrates, proteins and other food constituents, in which the fatty acids of the fats consist of:

—55–95 wt. % n-3 polyunsaturated chain fatty acids caprylic acid and capric acid, —5–25 wt. % of the medium chain fatty acids stearidonic acid, eicosatetraenoic acid, eicosapeataenoic acid, docosapentaenoic acid and/or docosahexaenoic acid, —0–30 wt. % of other fatty acids, is suitable for treating increased plasma lipid levels in hypertriglyceridaemia or hyperchylomicronaemia.

20 Claims, No Drawings

NUTRITIONAL COMPOSITION FOR THE TREATMENT OF HYPERTRIGLYCERIDAEMIA AND HYPERCHYLOMICRONAEMIA

FIELD OF THE INVENTION

The invention relates to a food composition, that is beneficial in lowering lipid levels in blood plasma. It is especially beneficial for persons suffering from hyperlipoteinaemia including hypertriglyceridaemia (HTG) and hyperchylomicronaemia.

BACKGROUND ART

The use of marine polyunsaturated fats as a supplement (6 g/day) has been proposed for the treatment of patients suffering from hypertriglyceridaemia (Sanders et al., *Arteriosclerosis*, 5 (5), 459–465 (1985)). The treatment resulted in a decrease in plasma triglyceride level in the patients.

DE-C-4417851 discloses a dietetic supplement (spread) containing a fat phase and a water phase, wherein the fat phase comprises 70–90% (80%) medium-chain fatty acids, 0.9–2.5% (1.6%) long-chain saturated fatty acids, 3.8–13.4% (9%) linoleic acid, 3–8% (5.4%) α-linolenic acid, 1–2.5% (1.8%) γ-linolenic acid and 1.3–3.6% (2.2%) oleic acid. This supplement is intended to be used for increasing the bioavailability of fats, which is required in patients having digestion problems with fat. Patients with increased lipids in the metabolic syndrome do not have problems with the intestinal digestion or absorption of fats. The supplement according to DE-C-4417851 is unsuitable as a nutritional composition for patients suffering from increased plasma lipid levels.

The enteral use of a food or drug component containing at least 5% of n-3 fatty acids and another food or drug component containing at least 5% of medium-chain triglycerides for improving glucose intolerance, insulin resistance or hyperlipidaemia is described in DE-A-195.03993. The food components should be presented in a masked or encapsulated form. No data on the administration levels of these fat components and on the importance of other components are given, and no clinical data showing the effect of the proposed use are presented.

EP-A-687418 discloses a fat blend consisting of about 25 wt. % of medium chain triglycerides, about 35 wt. % of a source of ω-6 fatty acids (soy oil) and about 40 wt. % of a source of ω-3 fatty acids (marine oil), which is proposed for the treatment of trauma, burns or sepsis. A total enteral composition according to this prior art contain 20 en. % of the fat blend, 20 en. % of protein and 50 en. % of carbohydrate.

A nutritional product containing 45–56 en. % of fat, wherein the fat comprises about 25 wt. % of medium chain triglycerides, about 20 wt. % of fish oil (stearidonic acid, EPA and DHA accounting for about 8 wt. %), about 25 wt. % of oleic acid and about 16 wt. % of linoleic acid, is described in WO 93/19624 as suitable for improving pulmonary function.

A similar product containing 45–60 en. % of fat, wherein the fat can comprise about 25 wt. % of medium chain triglycerides, about 8 wt. % of fish oil (EPA and DHA accounting for about 3 wt. %), about 45 wt. % of oleic acid and about 10 wt. % of linoleic acid, is described in EP-A-6111568 for the treatment of cancer.

SUMMARY OF THE INVENTION

The invention aims at providing a food composition better suitable for treating increased plasma lipid levels in the metabolic syndrome than the prior art compositions.

The invention furthermore aims at providing a method for treating increased plasma lipid levels in various diseases which are associated with the metabolic syndrome.

The composition according to the invention is characterized by a particular fat composition as defined in the appending claims. Per 100 g fatty acids of the fat, the composition of the invention comprises:
— from 55 up to 95 g, preferably from 65 or even from 70 up to 90 g, especially about 75–80 g, of medium-chain fatty acids (MCFA's), i.e. C8 (caprylic acid) and C10 (capric acid), and
— from 5 up to 25 g, preferably 7–20 g, especially 8–15 g, of n-3 poly-unsaturated fatty acids (n-3 PUFA's).

The method of the invention comprises administering the composition described above to a person suffering from increased plasma lipid levels.

DETAILED DESCRIPTION OF THE INVENTION

A novel food composition has been found which is useful as a supplement, but especially as a complete food, suitable for the treatment of increased plasma lipid levels, especially above 200 mg/dl. The composition is useful in the treatment of various diseases which can be associated with the metabolic syndrome (syndrome X), such as hyperlipoproteinaemia—including elevated VLDL levels, hypercholesterolaemia, hyperchylomicronaemia and especially hypertriglyceridaemia (HTG)—obesity, hyperuricaemia, hypertension, fatty liver, diabetes type II (non-insulin-dependent diabetes mellitus), insulin resistance and atherosclerotic vascular diseases.

The fat composition comprises a major amount (55–95 % by weight) of medium-chain, especially C8 and C10, fatty acids (MCFA's) and a substantial amount (5–25 % by weight of n-3 polyunsaturated fatty acids (n-3 PUFA's).

It was found that if the amount of fatty acids other than MCFA's (C8:0 and C10:0) and n-3 PUFA's (C18:4, C20:4, C20:5, C22:5 and C22:6), which other fatty acids include essentially all normal fatty acids, is exceptionally low, i.e. below 30 g, preferably below 20 g, and most preferably below 15 g, or even below 12 g per 100 g of fatty acids of the fat, the overall effect of the composition is especially favorable.

Preferably the amounts of docosahexaenoic acid (DHA, cervonic acid) and eicosapeiitaenoic acid (EPA) are about equal (DHA/EPA=0.2–2), and their combined amount is at least 5%, more preferably at least 8 wt. % of the fatty acid composition.

For some situations it is useful to include an amount of linoleic acid; this amount should preferably not exceed 8 g per 100 g of fatty acids and is especially 0.2–3.8 wt. %. The ratio between the n-3 PUFA's and the n-6 PUFA's (predominantly linoleic acid) preferentially has a value between 1.5 and 25, more preferably between 2 and 15, especially between 2 and 8.

The following definitions apply:
— Medium chain fatty acids (MCFA): aliphatic carboxylic acids having 8 or 10 carbon atoms, in particular C8 (caprylic acid) and C10 (capric acid) alkanoic acids.
— n-3 (or ω-3) Polyunsaturated long-chain fatty acids (n-3 PUFA's): any carboxylic acid having at least 18 carbon atoms and having at least 4 non-conjugated cis-unsaturated bonds, the distal one of which from the carboxyl group being located between the ω-3 and ω-2 carbon atoms; these are in particular stearidonic acid (SDA, C18:4), eicosatetraenoic acid (ETA, C20:4), eicosapentaenoic acid (EPA, C020:5), docosapentaenoic acid (DPA, C22:5), and docosahexaenoic acid (DHA, C22:6); for the purpose of the invention, α-linolenic acid (ALA, C18:3) is not counted among the n-3 PUFA's.

—n-6 (ω-6) Polyunsaturated long-chain fatty acids (n-6 PUFA's): any carboxylic acid having at least 18 carbon atoms and having at least 2 non-conjugated cis-unsaturated bonds, the distal one of which from the carboxyl group being located between the ω-6 and ω-5 carbon atoms; these are in particular linoleic acid (C18:2), γ-linolenic acid (GLA, C18:3), dihomo-γ-linolenic acid (DGLA, C20:3), and arachidonic acid (ADA, C20:4), especially linoleic acid.

—Other fatty acids; any fatty acid other than the MCFA's (C8 and C10) and the n-3 PUFA's (SDA, ETA, EPA, DPA and DHA); these include therefore the n-6 PUFA's, α-linoleic acid, and all monounsaturated and saturated fatted acids of more than 10 carbon atoms, such as lauric, myristic, palmitic, palmitoleic, stearic, oleic, eicosenoic and docosenoic (erucic) acid.

—Energy percentage (en. %): the theoretical contribution of a component to the energy content of the composition, assuming complete digestibility and assuming a specific energy of 9.0 kcal/g for fats and 4.0 kcal/g for carbohydrates and proteins.

The total fat content of the complete nutritional compositions according to the invention is high: it may vary from 33 to 63 en. % (energy%), preferably 48–60 en. %.

The food composition will further comprise a relatively low content of carbohydrates of 15–40 en. %, and preferably 20–35 en. %.

The product is further designed to provide an amount of energy that allows the patient to fulfill daily activities. The amount of calories that is administered may vary between 700 and 3000 kcal per day, but is preferably in the range of 1500–2500 kcal/day.

In order to facilitate food consumption the energy density may be relatively high. Good results are obtained with an energy, density of about 1.0 kcal/ml, but for some patients with the metabolic syndrome, the energy density should be above 1.2 kcal/ml, for example in the range 1.3–1.6 kcal/ml.

The protein level results from the levels of fat and carbohydrates and, when applicable, the other constituents like fibre and minerals. Amounts vary between 5 and 30 en. % and are typically 10–20 en. %.

Other components may be included as well. A list can be found in table 1. Other components include (per 2000 kcal): fibre 0–40 g (preferably 30 g), choline 100–1000 mg (preferably, 400 mg), possibly as lecithins, carnitiine 50–500 mg (preferably 200 mg), carotenoids 0.2–7 mg, preferably 1.0 mg β-carotene, and lipoic acid.

Other additives such as stabilizers and antioxidants, emulsifiers and taste improving substances like flavorings from natural origin (fruits) or nature-identical flavorings and citric acid can also be included. Tocopherols, tocotrienols, ascorbates, as well as synergetically acting mixtures (like a combination of vitamin C, vitamin E and lecithin) as known in the art, can be used as antioxidants. Raw ingredients or fractions thereof such as palm kernel oil, fruit extracts, or plant extracts like rosemary extract, can also be used as a source of antioxidants, vitamins or lecithin.

Production:

Raw ingredients that can be used during manufacture are protein sources like skimmed milk powder, whey powder, caseins, and vegetable proteins like those from soy, pea etc. and mixtures of these proteins or their hydrolysates. The protein composition is chosen in such a way that supply of the recommended daily amounts of amino acids is ensured.

The levels of some amino acids like methionine, glutamine, arginine, tyrosine or tryptophan may be modified to meet specific nutritional needs for this group of patients.

As fat sources can be used: MCT (medium-chain triglyceride) oil, preferably predominantly consisting of capry,lic and capric fats; a satisfactory effect is achieved if, in addition to the MCFA's defined above, minor amounts of lauric acid (C12) are used, the level of lauric acid preferably being below 10% of the total of C8,C10 and C12 fatty acids; even better results are obtained when the sum of MCFA's (C8 and C10) is above 97% of the sum of C8,C10 and C12. Fish, microbial and/or egg lipids can be used as sources of eicosapentaenoic acid and/or docosahexaenoic acid and other n-3 PUFA's. Egg oil (like n-3 FA enriched egg lecithins), safflower oil or other vegetable oils (like specific palm kernel oils) can be used as a source of linoleic acid. The sources of fats are selected in such a way, that the resulting levels of long chain fatty acids other than SDA, ETA, EPA, DPA and DHA are as low, as possible.

For example, for a daily consumption of 2000 kcal, a mixture of 9–45, in particular 15–27 g of 55% fish oil, or 6.5–32, in particular 10–19 g of 80% fish oil, and 80–110 g (in case of 55% fish oil) or 87–112 g (in case of 80% fish oil) of MCT fats, can used as fat mix.

Suitable sources of carbohydrates include an type of starch, maltodextrin or (oligo)saccharide or mixture thereof that gives a relatively small rise in plasma lipid or insulin levels. In practice this means that carbohydrate sources are used that have low contents of mono- and disaccharides. The level of mono- and disaccharides in the composition is preferably below 5 wt. % with respect to the dry matter of the composition. Preferably, part of the carbohydrates used is slowly digestible.

Fibre that can be used in the present composition comprises any ingredient or mixture of ingredients that provides a healthy gut flora, for example the fibre blend that is described in European patent application 756828. Such fibres may include soluble non-starch polysaccharides such as long-chain insulin, pectin and the like, insoluble non-starch polysaccharides such as cellulose and hemicellulose, non-digestible oligosaccharides such as short-chain insulin and galacto-oligosaccharides, resistant starch and lignin. Also fibres can be used that decrease the bioavailability of mono- and disaccharides such as certain types of gums.

Vitamins, minerals and trace elements can be used from all physiologically acceptable sources (like the pharmaceutical salts of trace elements that are permitted for use as food ingredient). An example is given in table 1.

Complete foods are preferred. However, supplements containing 55–95 wt. %, especially 65–90 wt. %, of MCFA's, 5–25 wt. %, especially 8–15 wt. %, of n-3 PUFA's and less than 30 wt. %, especially less than 20 wt. %, of other fatty acids, are also comprised by the invention. Tube feedings having the composition as described above form a preferred embodiment of the present invention. The food may also be a drink with a nice taste, or a powder that can be reconstituted to produce such a drink. The nutritional composition can be used in the treatment of increased plasma lipid levels, suitably in combination with the administration of drugs, such as fibrates (e.g. Normalip Pro®).

The nutritional composition can be a liquid having an energy density of at least 1.0 kcal/ml, preferably 1.3–1.6 kcal/ml. It can also advantageously be a powder containing 22–42 wt. %, preferably 28–38 wt. % of fat, 25–60 wt. %, preferably 30–50 wt. % of carbohydrates and 10–40 wt. %, preferably 15–30 wt. % of proteins, as described above. The product can be manufactured according to procedures as known in the art.

TABLE 1

Amounts of minerals, trace elements and vitamins that can be included in the composition according to the invention

| Component | Range per 2000 kcal | Preferred range per 2000 kcal | Example per 2000 kcal | Unit |
|---|---|---|---|---|
| vit A | 600–1800 | 800–1200 | 1000 | μg |
| vit D (3) | 2.5–15 | 8–13 | 10 | μg |
| vit E | 60–800 | 150–300 | 220 | mg |
| vit K1 | 30–300 | 80–180 | 130 | μg |
| vit B1 | 0.8–12 | 1.2–2.0 | 1.6 | mg |
| vit B2 | 0.8–12 | 1.6–4.0 | 2.7 | mg |
| niacin | 10–80 | 15–25 | 20 | mg |
| vit B6 | 1–50 | 2–6 | 4 | mg |
| vit C | 40–800 | 50–250 | 200 | mg |
| vit B12 | 3–30 | 5–9 | 7 | μg |
| folic acid | 100–900 | 300–500 | 400 | μg |
| pantothenic acid | 6–100 | 8–20 | 14 | mg |
| biotin | 70–280 | 80–160 | 120 | μg |
| Na | 700–3500 | 1500–2500 | 2000 | mg |
| K | 300–6000 | 2000–4000 | 3000 | mg |
| Mg | 180–1500 | 300–600 | 450 | mg |
| Ca | 600–2100 | 1000–1600 | 1300 | mg |
| P | 300–1200 | 500–1100 | 800 | mg |
| Se | 30–300 | 50–150 | 90 | μg |
| Cl | 1100–7000 | 3000–4500 | 3600 | mg |
| F | 0.5–10 | 1–4 | 2.5 | mg |
| Fe | 4–40 | 12–26 | 18 | mg |
| Zn | 5–35 | 10–200 | 15 | mg |
| Cu | 1000–5000 | 2000–3200 | 2500 | μg |
| Mn | 2000–12000 | 2300–3600 | 2800 | μg |
| I | 150–1500 | 150–300 | 225 | μg |
| Mo | 60–500 | 200–300 | 250 | μg |
| Cr | 30–700 | 150–300 | 225 | μg |

A surprising feature of the present compositions, especially of complete food compositions, is that, despite the highly unusual combination of components, the present compositions are well tolerated and accepted, whereas prior art compositions proposed for comparable indications frequently, lead to intolerance, unwanted side-effects.

EXAMPLE

A fat composition obtained by mixing 40.8 kg of MCT oil, 3.3 kg of soy oil, 9.0 kg of fish oil (containing 32% of EPA and 28% of DHA) and 2.8 kg of lecithin, having the fatty acid composition (wt. %) as listed in table 2, was mixed with an aqueous phase containing 21 kg of calcium casceinate and 21 kg of sodium caseinate (90% proteins), 87 kg of maltodextrins and 3.7 kg of other minerals, vitamins and trace components according to table 1 per 1000 l of final composition. The dry substance composition (wt. %) is 46% carbohydrates, 20% proteins and 29.6 % fats.

The composition was administered by tube feeding to 22 patients suffering from hypertriglyceridaemia (plasma levels above 400 mg/dl) for 7 days at a rate of 1500 ml/day. The administration was accepted without any tolerance or other problem. The average triglyceride plasma level dropped from 1300 mg/dl on day 1 to 380 mg/dl on day 7; over the same period, the average total cholesterol level decreased from 420 to 290 mg/dl.

TABLE 2

| Fatty acid composition of fat mixture in weight % | |
|---|---|
| caprylic (C8) | 46.6 |
| capric (C10) | 28.2 |
| linoleic (ω6-C18:2) | 3.6 |
| SDA (ω3-C18:4) | 0.2 |
| ETA (ω3-C20:4) | 0.3 |
| EPA (ω3-C20:5) | 5.7 |
| DPA (ω3-C22:5) | 0.9 |
| DHA (ω3-C22:6) | 4.9 |
| other | 9.6 |
| total MCFA's | 74.8 |
| total n-3 PUFA's | 12.0 |
| total other | 13.2 |
| DHA:EPA | 0.86 |
| n-3:n-6 | 3.1 |

We claim:

1. A nutritional composition suitable for the treatment of increased plasma lipid levels in hypertriglyceridaemia or hyperchylomicronaemia, comprising fats, the fatty acids of said fats comprising:
   —55–95 wt. % of medium chain fatty acids (MCFA's);
   —5–25 wt. % of n-3 polyunsaturated fatty acids (n-3 PUFA's);
   —0–30 wt. % of other fatty acids.

2. A nutritional composition according to claim 1, wherein the fatty acids comprise:
   —65–90 wt. % of MCFA's;
   —8–15 wt. % of n-3 PUFA's; and
   —0.2–15 wt. % of other fatty acids.

3. A nutritional composition according to claim 1, wherein the fat composition comprises at least 4 g up to 10 g of eicosapentaenoic acid and at least 4 g up to 10 g docosahexaenoic acid per 100 g of fatty acids.

4. A nutritional composition according to claim 1, wherein said other fatty acids comprise 0.2–8 wt. % of linoleic acid.

5. A nutritional composition according to claim 4, wherein said other fatty acids comprise 0.2–3.8 wt. % of linoleic acid.

6. A nutritional composition according to claim 1, wherein the weight ratio between the sum of n-3 PUFA's and the sum of n-6 PUFA's is between 1.5 and 25.

7. A nutritional composition according to claim 6, wherein the weight ratio between the sum of n-3 PUFA's and the sum of n-6 PUFA's is between 2 and 8.

8. A nutritional composition according to claim 1, wherein the composition is a complete food, further comprising carbohydrates and proteins, the fats comprising 33–63 energy %, the carbohydrates comprising 15–40 energy % and the proteins comprising 5–30 energy % of the composition.

9. A nutritional composition according to claim 8, the fats comprising 48–60 energy %, the carbohydrates comprising 20–35 energy % and the proteins comprising 10–20 energy % of the composition.

10. A nutritional composition according to claim 8, which contains 700–3000 kcal in a daily dosage unit.

11. A nutritional composition according to claim 10, which contains 1500–2500 kcal in a daily dosage unit.

12. A nutritional composition according to claim 8, which is a liquid having an energy density of 1.0–2.0 kcal/ml.

13. A nutritional composition according to claim 12, which is a liquid having an energy density of 1.3–1.6 kcal/ml.

14. A nutritional composition according to claim 8, which is a powder containing 22–42 wt. % of fat, 25–60 wt. % of carbohydrates and 10–40 wt. % of proteins.

15. A nutritional composition according to claim 14, which is a powder containing 28–38 wt. % of fat, 30–50 wt. % of carbohydrates and 15–30 wt. % of proteins.

16. A method for the treatment of increased plasma lipid levels in hypertriglyceridaemia or hyperchylomicronaemia, comprising administering to a person in need thereof a nutritional composition comprising fats, the fatty acids of said fats comprising:

—55–95 wt. % of medium chain fatty acids (MCFA's);
—5–25 wt. % of n-3 polyunsaturated fatty acids (n-3 PUFA's);
—0–30 wt. % of other fatty acids.

17. A method according to claim 16, wherein the fatty acids comprise at least one of:
—65–90 wt. % of MCFA's;
—8–15 wt. % of n-3 PUFA's; and
—0.2–15 wt. % of other fatty acids.

18. A method according to claim 16, wherein said other fatty acids comprise 0.2–8 wt. % of linoleic acid.

19. A method according to claim 16, wherein the weight ratio between the sum of n-3 PUFA's and the sum of n-6 PUFA's is between 1.5 and 25.

20. A method according to claim 16, wherein the composition is a complete food, further comprising carbohydrates and proteins, the fats comprising 33–63 energy %, the carbohydrates comprising 15–40 energy % and the proteins comprising 5–30 energy % of the composition.

* * * * *